United States Patent
Carrel et al.

(10) Patent No.: US 10,420,900 B2
(45) Date of Patent: Sep. 24, 2019

(54) PROTECTION DEVICE FOR PROTECTING AN INJECTION NEEDLE

(71) Applicant: Becton Dickinson France S.A.S., Le Pont-de-Claix (FR)

(72) Inventors: Franck Carrel, Saint Jean de Vaulx (FR); Laurent Barrelle, Saint Nizier du Moucherotte (FR)

(73) Assignee: Becton Dickinson France S.A.S., Le Pont-de-Claix (FR)

( * ) Notice: Subject to any disclaimer, the term of this patent is extended or adjusted under 35 U.S.C. 154(b) by 163 days.

(21) Appl. No.: 15/251,469

(22) Filed: Aug. 30, 2016

(65) Prior Publication Data

US 2016/0367765 A1 Dec. 22, 2016

Related U.S. Application Data

(62) Division of application No. 11/912,257, filed as application No. PCT/IB2006/001738 on Apr. 20, 2006, now Pat. No. 9,457,157.

(30) Foreign Application Priority Data

Apr. 20, 2005 (FR) ...................... 05 03965

(51) Int. Cl.
    *A61M 5/32* (2006.01)
    *A61M 5/36* (2006.01)

(52) U.S. Cl.
    CPC .......... *A61M 5/3272* (2013.01); *A61M 5/326* (2013.01); *A61M 5/36* (2013.01); *A61M 2005/3267* (2013.01)

(58) Field of Classification Search
    CPC .. A61M 5/321; A61M 5/3243; A61M 5/3245; A61M 5/326; A61M 5/3271;
(Continued)

(56) References Cited

U.S. PATENT DOCUMENTS 5,254,099 A    10/1993    Kuracina et al.
5,984,899 A *    11/1999    D'Alessio ........... A61M 5/3271
                                                                               604/192
(Continued)

FOREIGN PATENT DOCUMENTS

WO           9111212 A1    8/1991

*Primary Examiner* — Kami A Bosworth
(74) *Attorney, Agent, or Firm* — The Webb Law Firm

(57) ABSTRACT

The present invention relates to a protection device (1) intended to at least partially cover the needle (2) of an injection device, comprising: a support (3) of the protection device (1), a sleeve (4) movable axially in translation with respect to the support (3), an arrangement (14) for returning the sleeve (4) from an injection position to a protection position, an axial guidance arrangement (29, 30) for preventing the sleeve (4) from pivoting with respect to the support (3), one peg (6) directly and at least elastically, coupled longitudinally to the support (3) or the sleeve (4) and housed in a passageway (10) defining a first section (11) and a second section (12) followed by the peg (6) from a storage position to the injection position and then to the protection position, and a safety arrangement (21; 36, 34, 35) part of which being elastically deformable, arranged in a way as to prevent the peg from returning from the second section to the first section. The invention also relates to packaging (26) for the device.

10 Claims, 5 Drawing Sheets

(58) Field of Classification Search
CPC ........ A61M 5/3272; A61M 2005/3247; A61M 2005/3267
See application file for complete search history.

(56) References Cited

U.S. PATENT DOCUMENTS

| | | |
|---|---|---|
| 6,485,469 B1 | 11/2002 | Stewart et al. |
| 2002/0004648 A1 | 1/2002 | Larsen et al. |
| 2002/0004652 A1 | 1/2002 | Asbaghi |
| 2003/0093035 A1 | 5/2003 | Mohammed |
| 2004/0111064 A1 | 6/2004 | Asbaghi |
| 2004/0127857 A1* | 7/2004 | Shemesh ............... A61M 5/326 604/198 |
| 2004/0230158 A1 | 11/2004 | Malenchek |
| 2005/0113750 A1* | 5/2005 | Targell .................. A61M 5/326 604/110 |

* cited by examiner

PROTECTION DEVICE FOR PROTECTING AN INJECTION NEEDLE

CROSS REFERENCE TO RELATED APPLICATION

This application is a divisional application of U.S. patent application Ser. No. 11/912,257, filed Sep. 12, 2008, now U.S. Pat. No. 9,457,157, which is a U.S. National Stage application of International Application No. PCT/IB2006/001738, filed Apr. 20, 2006, which claims priority to French Application No. 0503965, filed Apr. 20, 2005, the entire disclosures of each of which are herein incorporated by reference.

FIELD OF THE INVENTION

The present invention relates to a protection device for protecting a needle so as to protect the patient and/or the user from the risk of needlestick injury, particularly after the said needle has been used.

BACKGROUND OF THE INVENTION

In the medical field, syringes may be supplied ready for use or in the form of kits to be assembled, which may or may not be pre-filled with the liquid that is to be injected. Thus, the liquid that is to be injected is often supplied within a syringe body containing the dose that is to be injected. The end of the syringe body may be provided directly with a needle or may be provided with a syringe tip to which a needle support bearing the needle can be fixed. This syringe tip is, for example, of the "luer" or "luer lock" type. These syringes, syringe tips and needle supports are preferably "single-use" items so as to limit the risk of contaminating the patients and/or the care personnel with equipment that has already been used.

In this field, it is also of prime importance that the patients and users be protected from any risk of needlestick injury, particularly between the moment that injection is finished and the discarding of the injection device. Sleeves that protect the needles and that are activated manually after injection exist but in order to render the operation of protecting the needle more reliable and easier for the user, attempts have been made to render automatic the placement of the protective sleeve around the needle at the moment the needle is withdrawn from the injection site.

Document EP 409 180 describes a device for protecting a needle comprising a moving sleeve intended to cover the needle after injection. However, this protection device entails the sleeve rotating on itself by a certain amount in order to trigger its deployment, this rotation being performed while the distal end of the sleeve is in contact with the patient's skin, and while the medicinal product is being injected.

Thus, in such a case, because of the rotating of the sleeve, an undesirable feeling of friction against the skin and/or of instability of the injection device is perceived by the patient and/or by the user. This results in a notable impediment to the giving of the injection. As the injection cannot then be administered under optimal conditions, the patient and/or the user are reluctant to use the safety devices concerned and this often causes them to put themselves in unsafe injecting conditions. This solution is therefore not satisfactory.

There therefore remains a need for a device for protecting a needle, without additional manual intervention on the part of the user and which does not give rise to an effect of friction against the patient's skin.

SUMMARY OF THE INVENTION

The present invention aims to satisfy this need by proposing a device for protecting a needle that is effective, reliable with safety operation not directly linked to friction specificities, easy to manufacture and to use, comprises a limited number of parts, can be activated after injection without additional manual intervention on the part of the user so as to cover the needle, the said needle protection device not giving rise to any effect of friction against the patient's skin and limiting the risks of needlestick injury. In order to increase the safety of the injection, the present invention is also aimed at proposing such a needle protection device that is irreversible, preventing access to the needle once it has been activated. The present invention is also aimed at proposing a needle protection device that can be used in any field of medicine, veterinary science and with any injection device such as, for example, syringes, catheters and any other equivalent device.

The present invention relates to a protection device intended to at least partially cover the needle of an injection device, the said protection device comprising at least:
- a support provided with fixing means intended to secure the said protection device to an injection device,
- a sleeve comprising a distal end intended to come into contact with an injection surface and provided with an orifice intended to allow the said needle to pass, the said sleeve being arranged in such a way as to be moveable axially in translation with respect to the said support from a first position known as the storage position, in which the distal end of the said sleeve is at a distance $1_1$ from the said fixing means, to a second position known as the injection position, in which the distal end of the said sleeve is at a distance $1_2$ from the said fixing means, and to a third position known as the protection position, in which the distal end of the said sleeve is at a distance $1_3$ from the said fixing means, the said distances $1_1$ and $1_3$ being greater than the said distance $1_2$,
- first return means for returning the said sleeve at least from its injection position to its protection position, characterized in that the said protection device comprises at least:
- axial guidance means for guiding the said sleeve, arranged in such a way as to prevent it from pivoting axially as it moves axially with respect to the said support at least from its injection position to its protection position,
- at least one peg, directly and at least elastically, coupled longitudinally to the said support or to the said sleeve and housed in a running passageway provided respectively in the said sleeve or in the said support, the said running passageway forming more or less a U, of which the branches respectively define a first section taken by the said peg as the said sleeve moves from its storage position to its injection position and a second section taken by the said peg as the said sleeve passes from its injection position to its protection position, the said peg being designed to be laterally mobile,
- first safety means, at least part of them being elastically deformable, said first safety means being arranged in such a way as to prevent the said peg from returning from the said second section to the said first section.

The protection device according to the invention is able to protect efficiently the needle of an injection device, at least after injection. Particularly by virtue of the presence of a peg that can move laterally and which is longitudinally linked to the support, the impact of friction problem due to moving parts and that is encountered in other prior art protection devices, is avoided. Therefore, the protection device according to the invention is a more reliable protection device.

Furthermore, because the sleeve of the device according to the invention does not rotate on itself during the entire operation of administering the medicinal product, the injection is at no time disrupted by the effect of friction against the patient's skin, it is therefore easier and safer and can be administered without inconveniencing either of the patient or the user.

In addition, the protection device according to the invention makes it possible to avoid the risks of needlestick injury after injection as the needle is withdrawn from the injection site. What happens, after injection, as the injection device is withdrawn, is that the return means allow deployment of the sleeve without the user having to perform any additional manual operation. The operation of triggering the placement of the sleeve is therefore also safe.

The present invention also relates to an injection device comprising a needle protection device described hereinabove.

By virtue of the features of the invention, it is possible to supply an injection device ready for use and provided with the said protection device, it being possible for the end of the needle of the injection device to be visible, but nonetheless safe. Indeed, it may be important to nurses to have an injection device in which the end of the needle is visible: that allows them to expel air prior to most injections, with the best possible view of what they are doing. That also allows them better control over the first phase of the operation of injecting the medicinal product, namely the phase of positioning the needle on the injection site and orientating the tip of the needle with a view to inserting it and injecting the medicinal product.

In this application, the distal end of a component or a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

Within the meaning of this application, the "injection surface" may be the patient's skin in the case of an injection, the membrane of a bottle from which the product is taken or in which it is mixed, the end of a tube, of a pipe, the wall of a flexible bag, or of any connecting means.

The expression "able to move laterally" is to be understood, within the context of the current application, as meaning that the peg can move in a rectilinear or linear fashion in a plane perpendicular to the axis of the device, or in a circular fashion in a plane parallel to the axis of the device.

As a preference, the said axial-guidance means are arranged in such a way as also to prevent the said sleeve from pivoting axially as it moves axially with respect to the said support from its storage position to its injection position.

Advantageously, the said axial-guidance means comprise more or less complementary longitudinal geometric shapes provided respectively on the said sleeve and on the said support and arranged facing one another in order to collaborate. These geometric shapes may be grooves, ribs, bulges or alternatively slideways.

As a preference, the said first and second sections of the said running passageway are joined together by a first narrowed region defined by a flexible tongue at least partially defining the said first safety means.

Advantageously, the peg may be solid and made of a deformable material; it may be hollow, its walls deforming inwards, or may be formed of flexible tabs.

Advantageously, the said peg is urged laterally from the said first section towards the said second section by second return means at least partially defining the said first safety means.

As a preference, the said support or, respectively, the said sleeve comprises at least one tab able to deflect tangentially and bearing the said peg. Advantageously, the said tab is arranged in such a way as to deflect tangentially in an elastically deformable manner between a normal position and at least one stressed deflected position, said tab at least partially defining the said first safety means.

For example, the said tab is in a normal position or, respectively, in a stressed deflected position when the said peg is in the said first section, and the said tab is in the stressed deflected position or, respectively, in the normal position when the said peg is in the said second section. The said tab may be made of an elastically deformable material. The said tab may also comprise a pivot connection or a ball joint, which is elastically deformable, it being possible for this connection to be coupled to these return means.

As a preference, the said first and second sections have different lengths arranged in such a way as to delimit the said storage and protection positions such that the said distance $1_3$ is greater than the said distance $1_1$.

As a preference, facing the said running passageway provided on the said sleeve or, respectively, on the said support, the said support or, respectively, the said sleeve comprises a deflection passage arranged in such a way as to guide the said peg laterally.

In one embodiment of the invention, the said protection device comprises second safety means arranged in such a way as to block the said peg when the said sleeve is in the said protection position.

As a preference, the said second section of the said running passageway comprises a second narrowed region at least partially defining the said second safety means.

Advantageously, the said second section of the said running passageway comprises at least one step forming a stop catch for the said peg when the said sleeve is in the said protection position and at least partially defining the said second safety means.

In one embodiment of the invention, the said running passageway and/or the said deflection passage is formed of at least one element chosen from the group comprising a groove, a slot, a rib or a combination of these elements.

Advantageously, the said first and/or second return means are elastically deformable and chosen from the group comprising a helical spring, an elastic leaf, an elastically deformable element.

As a preference, the said first return means are arranged between the proximal end of the said support and the distal end of the said sleeve.

As a preference, the said sleeve or, respectively, the said support comprises at least one stop wall situated facing the said tab when the device is in the protection position, the said stop wall being arranged in such a way as to prevent the radial deflection of the said tab towards the axis of the said protection device in this protection position.

As a preference, the said support is provided with an injection needle.

The present invention also relates to an injection device comprising at least one injection needle and a reservoir of product that is to be injected, characterized in that it comprises at least one protection device as described hereinabove.

The present invention also relates to a set comprising a device as described hereinabove and packaging for this device, the said packaging comprising a cylindrical body and a cap, the said cylindrical body being equipped on its internal wall with means for blocking the rotation and translation of the said device within the said packaging.

BRIEF DESCRIPTION OF THE DRAWINGS

The present invention will now be described in greater detail with the aid of the attached drawings in which.

DETAILED DESCRIPTION OF THE INVENTION

Figure 1:
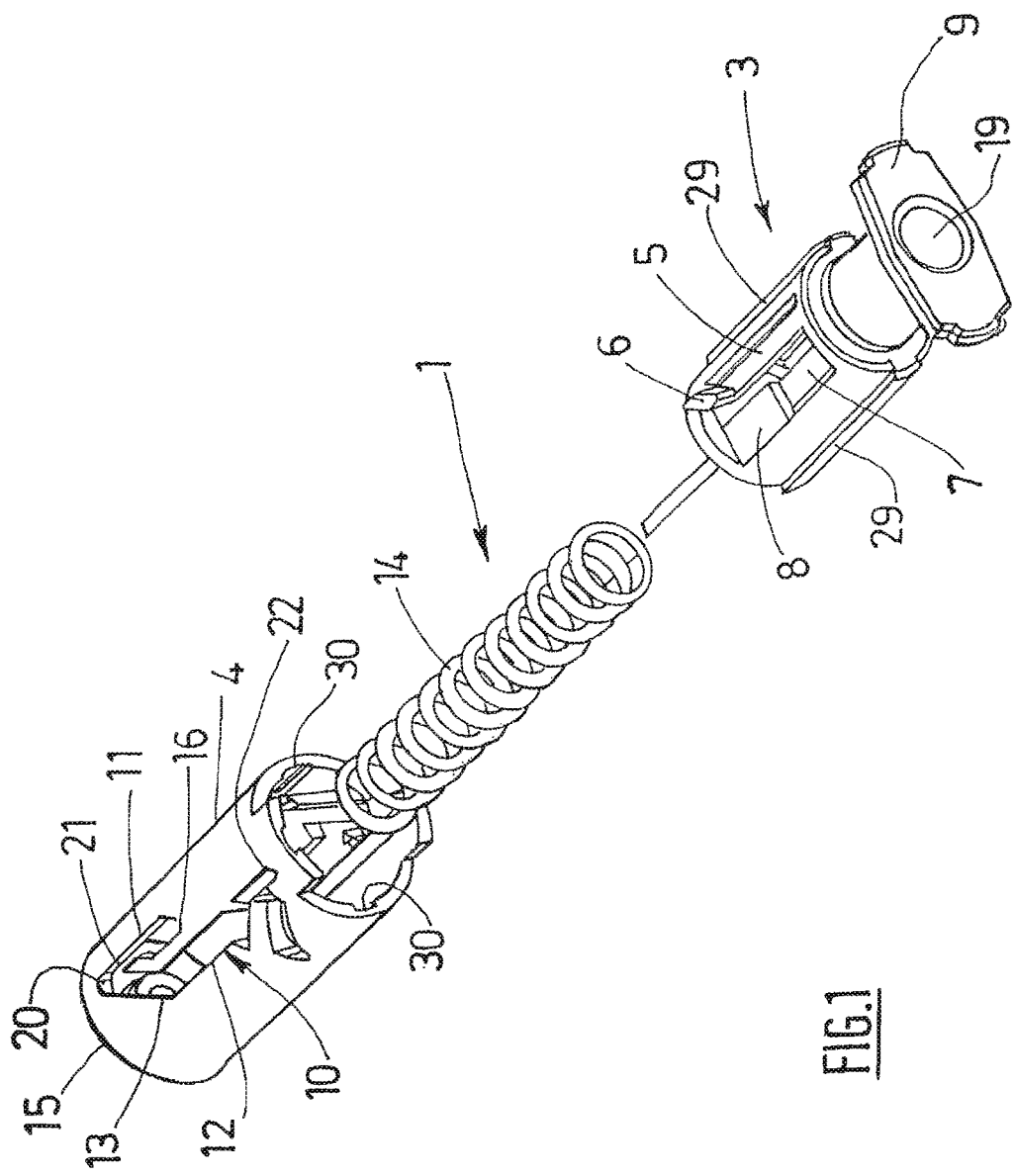
FIG. 1 is an exploded perspective view of the protection device according to the invention and of an end of a syringe body.

FIG. 1 depicts a protection device 1 for protecting an injection needle 2 according to the invention. This protection device 1 comprises a support 3 for a needle 2 and a sleeve 4 arranged in such a way as to accept the support 3. This sleeve 4 can be moved in translation with respect to the support 3, from a storage position depicted in FIG. 2 towards a second position, the injection position, depicted in FIG. 3 and towards a third position, the protection position, depicted in FIG. 4.

In the example depicted, the support 3 and the sleeve 4 each comprise means for the guidance and axial translation of the support 3 with respect to the sleeve 4: in FIG. 1, these guide means are in the form of diametrically opposed longitudinal bulges 29 situated on the external wall of the support 3, these longitudinal bulges 29 collaborating with diametrically opposed slideways 30 situated on the internal wall of the sleeve 4, facing the said bulges 29.

In FIG. 1, the support 3 comprises a flexible tab 5 which runs longitudinally from the proximal part of the support 3 in the distal direction. This flexible tab 5 at its distal end comprises a peg 6. This flexible tab 5 is able to deflect laterally between a normal position and at least one stressed deflected position (see FIG. 4). In FIG. 1, this flexible tab 5 is depicted in its normal position. Still in this figure, the tab 5 is able to move from its normal position to its stressed deflected position within a window 7 cut into the wall of the support 3. The support 3 comprises a stop wall 8 partially closing off the window 7, the function of which will be explained later on.

In FIG. 1, the support 3 comprises two proximal fins 9. These fins 9 may serve to block the rotation and translation of the device of the invention within its packaging (see FIG. 6) or to lock it in a standard "luer lock" connection system.

Figure 2:
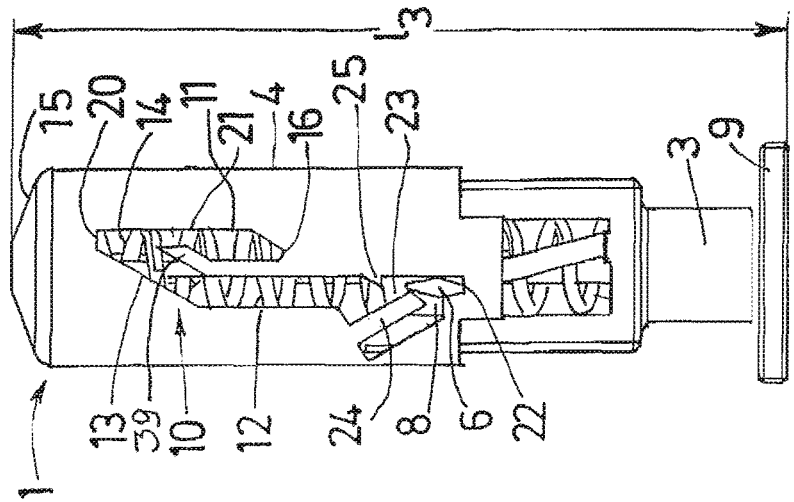
FIGS. 2 and 5 are, respectively, a side view and a view in section of the protection device of FIG. 1 in the storage position and of the end of an injection device.
Figure 3:
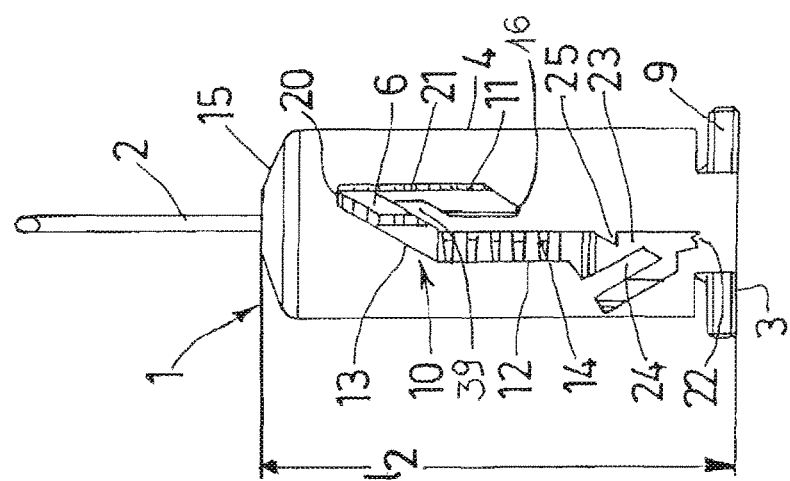
FIG. 3 is a side view of the protection device of FIG. 1, in the injection position.
Figure 4:
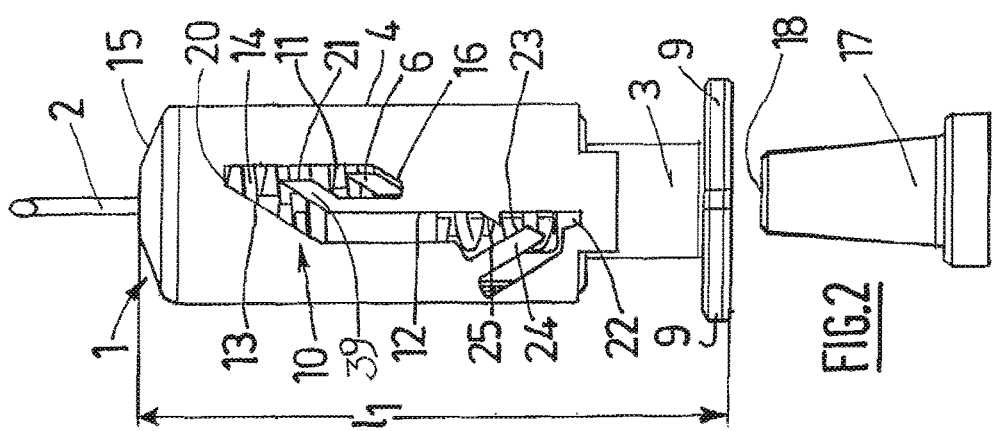
FIG. 4 is a side view of the protection device of FIG. 1 in the protection position.

In the example depicted, the sleeve 4 comprises a running passageway 10 forming a U, made in the wall of the sleeve 4 and arranged in such a way as to collaborate with the peg 6 over the entire travel of the sleeve, as will be apparent from FIGS. 2-4.

As can also be seen in FIGS. 2-4, the running passageway 10 comprises a first longitudinal section 11 and a second longitudinal section 12, which are more or less parallel and slightly angularly offset from one another about the longitudinal axis of the device 1. These two longitudinal sections 11 and 12 are connected to one another at their respective distal ends by an intermediate section 13.

As depicted in FIG. 1, the protection device 1 also comprises a helical spring 14. When the device 1 is assembled, as can be seen in FIG. 5, the proximal end 31 of this helical device 14 bears against an internal flange 32 of the proximal part of the support 3 and the distal end 33 of the spring 14 bears against the internal face of the radial distal wall 15 of the sleeve 4.

The way in which the protection device 1 according to the invention works will now be described with reference to FIGS. 2-4.

Figure 5:
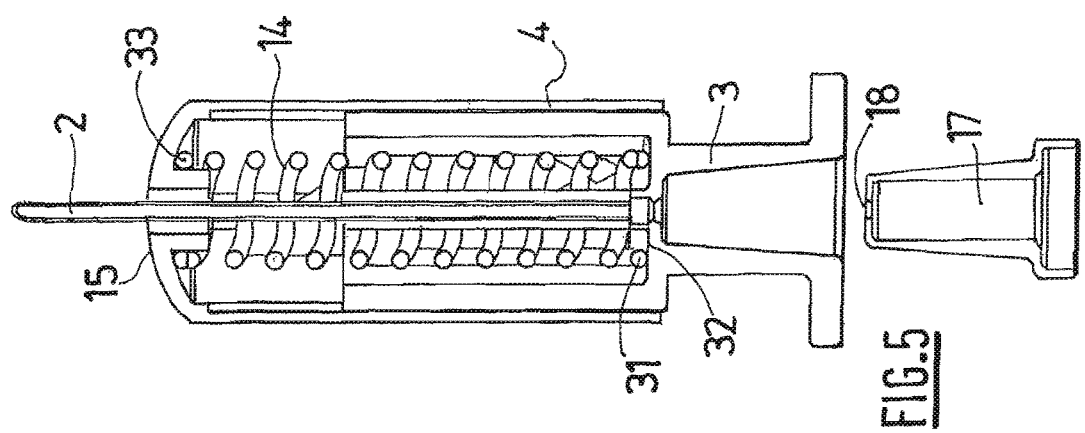

With reference to FIGS. 2 and 5, the protection device 1 is in the storage position. The sleeve 4 partially covers the needle 2. Thus, part of the needle 2 is visible for better user control both of the expelling of air and of the phase of positioning the needle 2 on the injection site prior to penetration.

In this storage position, the flexible tab 5 (partly concealed by the sleeve 4 in FIG. 2) is in the normal position and the peg 6 is kept in abutment against the proximal end 16 of the first longitudinal section 11 of the running passageway 10 by the action of the spring 14 which is partially compressed between the sleeve 4 and the support 3, as can be seen in FIG. 5.

The protection device 1 is therefore supplied for use in this storage position. The user then equips himself with the syringe body 17, partially depicted in FIG. 2, prefilled with the medicinal product to be injected into the injection site. This syringe body 17 comprises a standard distal tip 18 that can be fitted to the proximal base 19 (see FIG. 1) of the support 3 for connection to the needle 2. The user thus connects the syringe body 17 to the protection device 1 of the invention. For simplicity, the syringe body 17 will not be depicted in FIGS. 3 and 4.

Once the syringe body 17 is connected to the protection device 1, the user begins to cause the needle 2 to penetrate the injection site, until the distal radial wall 15 of the sleeve 4 comes into contact with the surface of the injection site and then he continues, via the syringe 17, to press on the support 3 in order to ensure complete penetration of the needle 2 in the injection site, the distal radial wall 15 of the sleeve 4 still being in contact with the surface of the injection site. The sleeve 4 therefore moves proximally in the axial direction with respect to the support 3 until the radial peg 6, which takes the path of the first longitudinal section 11, comes into abutment against the distal end 20 of this first longitudinal section 11.

The protection device 1 is then in the injection position as depicted in FIG. 3. In such a position, the spring 14 is in the compressed state and the needle 2 is exposed, that is to say not covered by the sleeve 4 because it is inside the injection site.

During the move from the storage position to the injection position, the sleeve 4 has not rotated on itself. The user then proceeds with injecting the medicinal product from the syringe body 17 in the known way, maintaining his pressure on the support 3, and the protection device 1 thus remains in the position depicted in FIG. 3.

At the end of injection, the user releases the pressure he was exerting on the support 3 via the syringe and proceeds to withdraw the needle 2 from the injection site, thus releasing the spring 14 which returns to its relaxed position carrying with it the support 3 which completely covers the needle 2. The flexible tab 5 and its radial peg 6 then take the path marked out by the intermediate section 13 and the second longitudinal section 12 of the running passageway 10, as shown in FIG. 4.

As can be seen in FIGS. 2-4, the first longitudinal section 11 comprises, situated proximally at its distal end 20, a narrowing 21 defined by a flexible tongue 39 which allows the peg 6 to pass in the distal direction and prevents the said peg 6 from returning in the proximal direction. In this embodiment, the flexible tongue 39 forms at least in part the first safety means, elastically deformable, preventing the peg 6 from returning from the said second section 12 to the said first section 11.

As the sleeve 4 deploys, when the peg 6 can follow the path marked out by the intermediate section 13 and the second longitudinal section 12 of the running passageway 10 by virtue of the ability of the tab 5 to deflect tangentially under stress.

For preference, the flexible tab 5 is made of a deformable and semi-rigid material such as polypropylene.

Thus, in the protection position as depicted in FIG. 4, the flexible tab 5 is in a stressed deflected position and the peg 6 is kept bearing against the proximal end 22 of the second longitudinal section 13 by the action of the spring 14 which is then in the at least partially relaxed position.

In order to block the protection device 1 in the protection position, the second longitudinal section 12 of the running passageway 10 comprises, situated distally at its proximal end 22, a narrowing 23 which allows the peg 6 to pass in the proximal direction and prevents the said peg 6 from returning in the distal direction. As a preference, the peg 6 or the narrowing 23 is able to deform elastically to allow this passing. There is thus no risk of the needle 2 re-emerging from the sleeve 4. In the example depicted, this narrowing 23 is obtained by the presence of two steps 24 and 25 situated facing one another on the second longitudinal section 12.

In the protection position, as depicted in FIG. 4, the peg 6 faces the stop wall 8 formed in the window 7 of the support 3. This stop wall 8 prevents the flexible tab 5 from deflecting radially towards the inside of the support: thus, it is not possible to separate the sleeve 4 from the support 3 and to re-expose the needle 2.

In an embodiment, not depicted, the second longitudinal section 12 of the running passageway 10 comprises a clearance space which is directed towards the first longitudinal section 11 and in which the peg 6 becomes blocked in a protection position in which the flexible tab 5 is partly or completely deflected.

In another undepicted embodiment of the invention, the flexible tab 5 is arranged on the sleeve 4 and the running passageway 10 is formed within the wall of the support 3. In yet another embodiment, not depicted, the flexible tab 5 is in a stressed deflected position when the protection device 1 is in the storage position and is in its normal position when the protection device 1 is in the protection position. In this embodiment, the flexible tab 5 forms at least in part the first safety means, elastically deformable, preventing the peg 6 from returning from the said second section 12 to the said first section 11.

In another embodiment of the invention, not depicted, the sleeve is inside the support.

Figure 6:
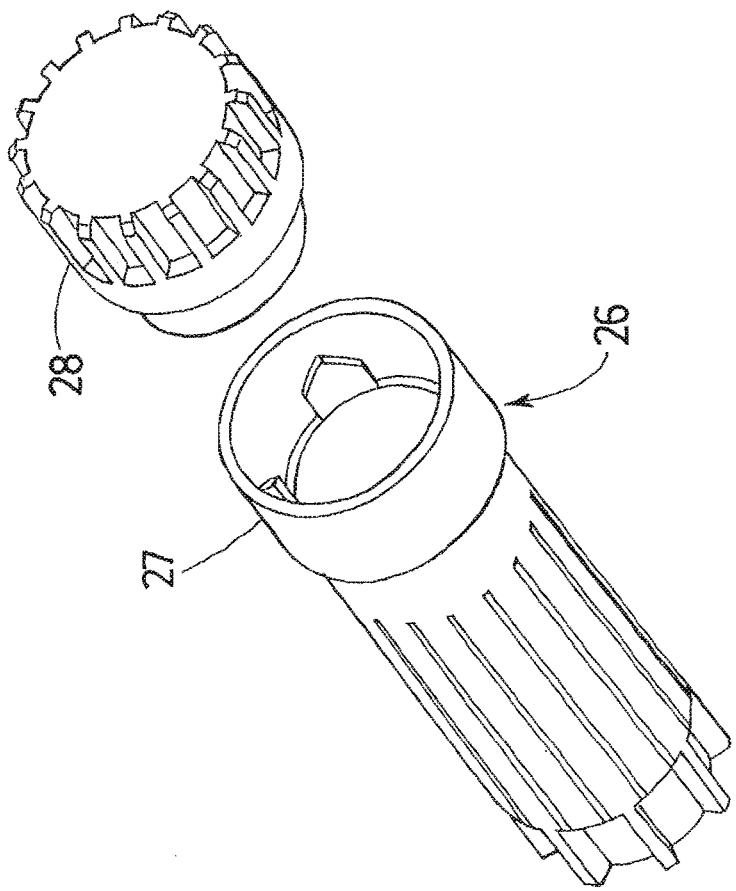
FIG. 6 is an exploded perspective view of packaging for the protection device of FIG. 1, FIGS. 7 to 9 are side views of a second alternative form of embodiment of the protection device according to the invention in the storage position, the injection position and the protection position respectively.

FIG. 6 depicts packaging 26 for the device 1 of the invention. Specifically, as the needle 2 is partially exposed when the protection device 1 is in the storage position, it is preferable for it to be supplied in protective packaging. The packaging 26 of FIG. 5 comprises a cylindrical body 27 and a cap 28. As a preference, the body 27 comprises, on its internal cylindrical wall, striations which collaborate with the fins 9 of the support 3 to prevent the device 1 from rotating within the packaging 26.

Figure 7:
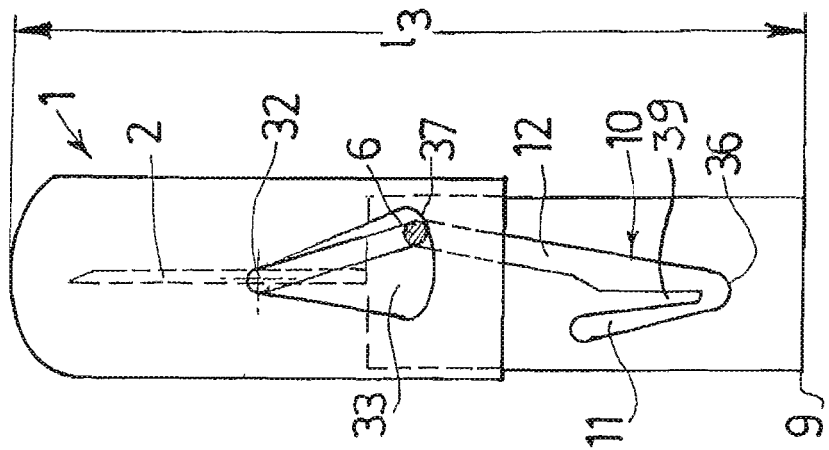
Figure 8:
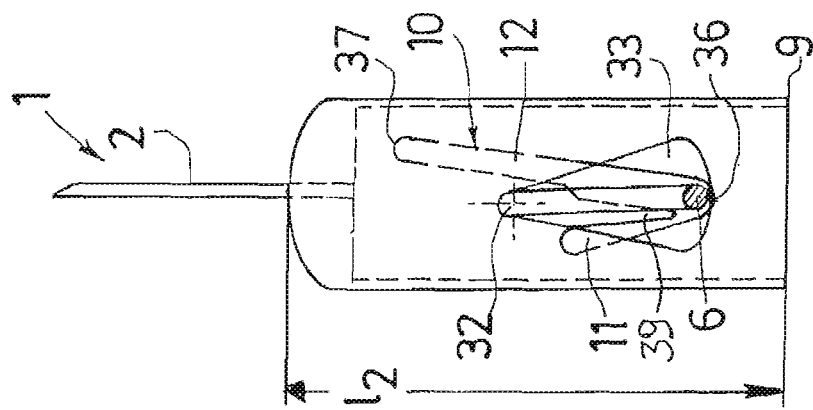
Figure 9:
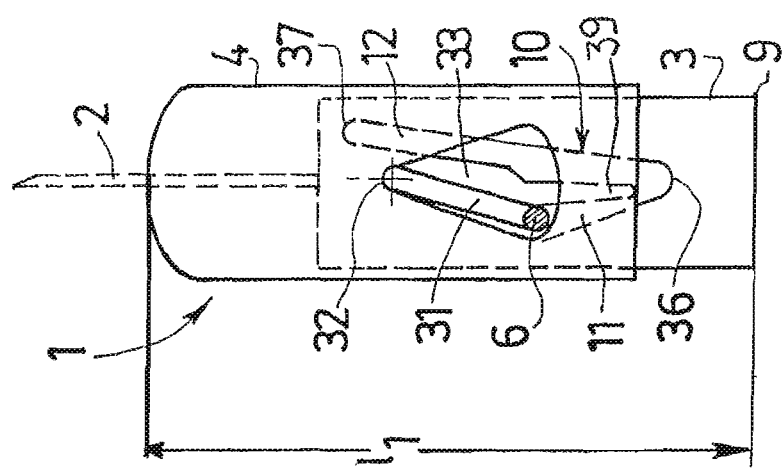

The protection device 1 of FIGS. 7 to 9 is similar to the device of FIGS. 1 to 6. It differs therefrom in that the running passageway 10 (depicted in dotted line in FIGS. 7 and 8 and partially in solid line in FIG. 9) is situated on the said support 3 and in that the flexible tab is replaced by a pivoting tab 31 equipped with a pivot connection 32, situated on the sleeve 4. The pivoting of the pivoting tab 31 occurs within a window 33 of triangular overall shape formed in the wall of the sleeve 4. The running passageway 10 is U-shaped, the second longitudinal section 12 of the U being longer than the first longitudinal section 11. Thus, the distance $l_3$ is greater than the distance $l_1$. The branches of the U are separated by a flexible tongue 39.

In the storage position, as depicted in FIG. 7, the peg 6 of the pivoting tab 31 is blocked in the distal end of the first longitudinal section 11 of the U forming the running passageway 10. Between the storage position and the injection position, the peg 6 is displaced along the first longitudinal section 11 where it presses against the flexible tongue 39 and bends it to reach the vertex 36 of the U. The flexible tongue 39 prevents the peg 6 from coming back to its storage position and forms at least part of the first safety means. In the injection position, as depicted in FIG. 8, the pivoting tab 31 has pivoted and the peg 6 is blocked in the vertex 36 of the U that forms the running passageway 10. In the protection position, as depicted in FIG. 9, the pivoting tab 31 has continued to pivot about the pivot connection 32 and the peg 6 is blocked in the second longitudinal section 12 of the U, e.g. at distal end 37, that forms the running passageway 10 by a narrowed region, not depicted.

In an undepicted embodiment of the invention, the pivoting tab does not move in a window; only the peg moves in a deflection passage.

In yet another undepicted embodiment of the invention, the sleeve has no window and the tab is superposed on the inside of the wall of the sleeve: thus neither the tab nor the peg move in a window.

The protection device 1 of FIGS. 10 to 14 is similar to the protection device of FIGS. 1 to 6. It differs therefrom in that the peg 6 is subject to the action of a spring 34 which is urged laterally from the first longitudinal section 11 towards the second longitudinal section 12 of the running passageway 10. The support 3 comprises a deflection passage 35 arranged in such a way as to guide the said peg 6 laterally.

Figure 10:
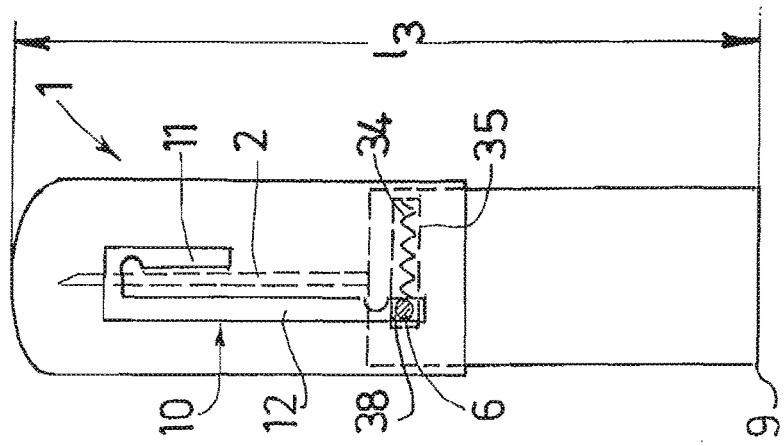
FIGS. 10 to 13 are side views of a third alternative form of embodiment of the protection device according to the invention in the storage position, the start-of-injection position, the end-of-injection position and the protection position, respectively.
Figure 14:
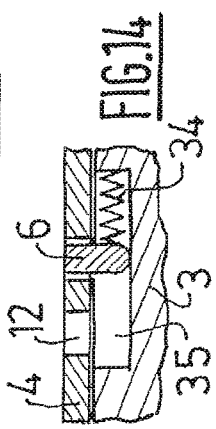
FIG. 14 is a partial sectioned view of the running passageway of the alternative form of embodiment of FIGS. 10 to 13.

Thus, in the storage position, as depicted in FIGS. 10 and 14, the peg 6 is blocked against the proximal end of the first longitudinal section 11 of the running passageway 10 because of the thrust of the spring 34 which is in the compressed state.

Figures 11, 12:
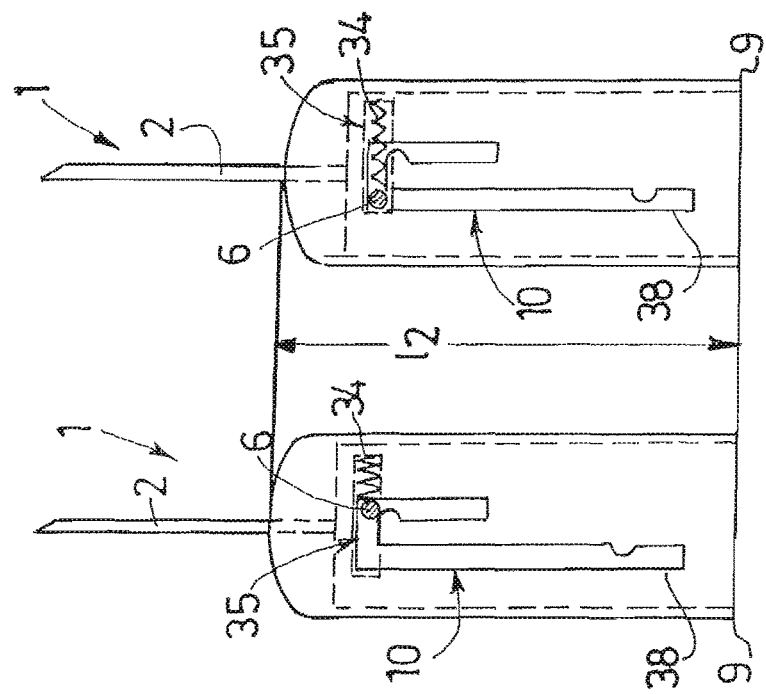

In the start-of-injection position, as depicted in FIG. 11, the peg 6 arrives in the deflection passage 35 in which it is pushed by the spring 34 which relaxes. In this embodiment, the spring 34 forms at least in part the first safety means, elastically deformable, preventing the peg 6 from returning from the said second section 12 to the said first section 11.

Figure 13:
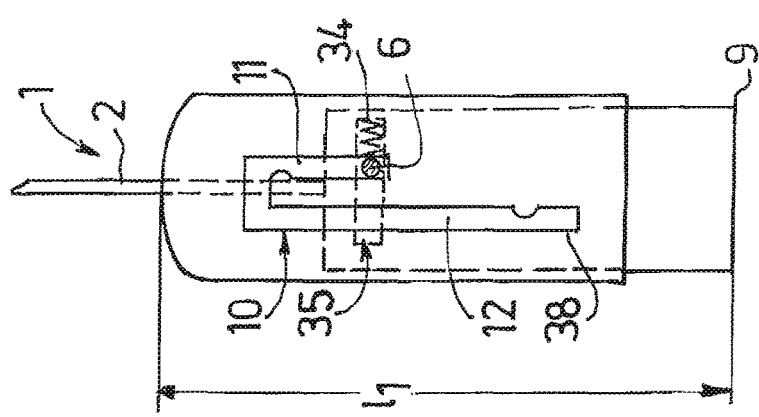

Thus, when the user withdraws the injection device 1 from the injection site, the peg 6 is guided in the second longitudinal section 12 of the running passageway 10. In the protection position, as depicted in FIG. 13, the peg 6 is kept blocked against the proximal end 38 of the second longitudinal section 12 of the running passageway 10 by the thrust of the spring 34. The needle is perfectly covered by the sleeve. The injection device 1 is safe.

As is apparent from the above description, the protection device 1 according to the invention allows an injection to be given in complete safety by virtue in particular of the fact that the sleeve 4 that protects the needle 2 does not rotate on itself at any time during the injection process and by virtue of the fact that this sleeve 4 deploys automatically at the end of the injection without any additional manual operation on the part of the user. In addition, the reliability of the protection device 1 according to the invention is increased by the reduced number of parts involved and their reduced relative movement with therefore enable to limit problems due to friction between moving parts.

What is claimed is:

1. A protection device at least partially covering a needle of an injection device, the protection device comprising:
   a support for the needle, wherein the support comprises a running passageway formed therein;
   a sleeve comprising a distal end intended to come into contact with an injection surface and provided with an orifice intended to allow the needle to pass therethrough, the sleeve being arranged so as to be moveable axially in translation with respect to the support between a storage position, an injection position, and a protection position; and
   a pivoting tab pivotally coupled to the sleeve about a pivot connection, the pivoting tab having a peg extending therefrom in a direction parallel to a pivot axis of the pivot connection, wherein the peg is configured to move within the running passageway of the support when the sleeve is translated axially with respect to the support between the storage position, the injection position, and the protection position.

2. The protection device of claim 1, wherein the running passageway is at least partially U-shaped.

3. The protection device of claim 2, wherein the at least partially U-shaped running passageway comprises a first longitudinal section and a second longitudinal section, the second longitudinal section laterally spaced from the first longitudinal section.

4. The protection device of claim 3, wherein the second longitudinal section is longer than the first longitudinal section.

5. The protection device of claim 3, wherein between the storage position and the injection position, the peg is displaced along the first longitudinal section of the running passageway.

6. The protection device of claim 3, wherein between the injection position and the protection position, the peg is displaced along the second longitudinal section of the running passageway.

7. The protection device of claim 3, wherein the first longitudinal section and the second longitudinal section are separated by a flexible tongue.

8. The protection device of claim 7, wherein the flexible tongue prevents the peg from moving from the second longitudinal section to the first longitudinal section.

9. The protection device of claim 2, wherein the peg is blocked in a vertex of the at least partially U-shaped running passageway when the sleeve is in the injection position.

10. The protection device of claim 1, wherein the pivoting of the pivoting tab occurs within a window of triangular overall shape formed in a wall of the sleeve.

* * * * *